United States Patent [19]

Hadbawnik et al.

[11] Patent Number: 4,930,892
[45] Date of Patent: Jun. 5, 1990

[54] PHOTODIODE ARRAY SPECTROMETER

[75] Inventors: Detlev Hadbawnik, Waldbronn; Karsten Kraiczek, Karlsbad, both of Fed. Rep. of Germany

[73] Assignee: Hewlett-Packard Company, Palo Alto, Calif.

[21] Appl. No.: 248,511

[22] Filed: Sep. 23, 1988

[30] Foreign Application Priority Data

Dec. 18, 1987 [EP] European Pat. Off. ........ 87118796.9

[51] Int. Cl.⁵ .............................................. G01J 3/18
[52] U.S. Cl. ................................................... 356/328
[58] Field of Search ............... 356/306, 307, 308, 326, 356/328, 329

[56] References Cited

U.S. PATENT DOCUMENTS

| | | | |
|---|---|---|---|
| 2,572,119 | 10/1951 | Dieke | 356/306 |
| 2,837,959 | 6/1958 | Saunderson et al. | 356/326 |
| 3,102,155 | 8/1963 | Vallee | 356/307 |
| 4,575,241 | 3/1986 | Demers et al. | 356/328 |

Primary Examiner—F. L. Evans

[57] ABSTRACT

A photodiode array spectrometer for determining the spectral composition of a plychromatic beam of radiation comprises diffraction means (10) which generate from the polychromatic beam a diffracted beam with a plurality of spatially separated diffracted rays of different wavelengths ($\lambda_1$, $\lambda_2$, $\lambda_3$). A photodiode array (11) receives the diffracted beam whereby each photodiode intercepts a different spectral portion of the beam. A rotatable transparent plate (8) is provided in the beam path in front of the diffraction means (10) which, due to refraction of the beam upon entering and leaving the plate (8), permits to vary the direction of the beam impinging on the diffraction means (10) and therefore the direction of the diffracted beam in small steps depending on the angle of rotation of the plate (8). By the stepwise displacement of the diffracted beam across the photodiode array (11), a better sampling of the diffracted beam and therefore an improved spectral resolution is achieved. The invention can be used in the spectrometric analysis of a sample contained in a sample cell (5), whereby the sample cell is irradiated with polychromatic light from a light source (1).

8 Claims, 6 Drawing Sheets

Fig. 1

FIG_1A

FIG_1B

FIG_1C

Fig. 2

PHOTODIODE ARRAY SPECTROMETER

The invention relates to a photodiode array spectrometer for determining the spectral composition of a polychromatic beam of radiation. Such spectrometers can be used, for example, for measuring the absorption spectrum of a sample substance in order to derive information about the chemical composition of the sample and the quantities of the individual constituents in the sample.

A photodiode array spectrometer is known from "A High-Speed Spectrophotometric LC Detector", Hewlett-Packard Journal, April 1984. This known spectrometer is used in a liquid chromatograph for analysing the substances eluting from the chromatographic column. The known detector comprises a light source emitting a broad spectrum of ultraviolet and visible radiation and an optical system for focusing the beam onto a sample cell through which the sample substances to be analysed flow. Depending on the specific substances flowing through the cell, the sample absorbs certain characteristic spectral portions of the radiation entering the sample cell so that the spectral composition of the radiation leaving the cell is indicative of the sample substances.

In the known spectrometer, the spectrum of the radiation leaving the sample cell is derived by means of a diffraction grating arranged in the optical path behind the cell. The diffraction grating directs light rays of different wavelengths into different directions. A linear array of photodiodes is arranged to receive the light diffracted by the grating. Each diode thus receives light corresponding to a different wavelength range. The electrical signals produced by the impinging light in each photodiode are read out by a read-out circuit and converted to digital data values which are representative of the intensity of the light impinging on the specific diode. These data values are then displayed as a function of wavelength in any convenient form, for example on a CRT screen. Since all the photodiodes of the array can be read out within a very short time interval, typically in the range of milliseconds, it is possible to produce spectra representative for the contents of the sample cell at a specific point in time, although the liquid is continuously flowing through the cell.

An important criterion for the quality of a spectrum is the spectral resolution, which indicates how well radiation components with closely adjacent wavelengths are separated so that they can be identified as separate components. The resolution of a photodiode array spectrometer depends on various factors, e.g., the width of the entrance slit of the spectrometer, the grating constant of the diffraction grating, and the number of photodiodes per unit length in the photodiode array. Typically, the photodiode array is the element in a photodiode array spectrometer which limits the resolution most. Although the resolution could theoretically be increased by increasing the number of photodiodes per unit length and by decreasing the space between adjacent photodiodes, there are practical limits to the "packing density" of photodiodes. As a result thereof, the resolution of the known photodiode array spectrometer is limited and the achievable resolution is not satisfactory for some applications.

Relative to this prior art, it is an object of the invention to provide a photodiode array spectrometer which has an improved spectral resolution.

According to an underlying principle of the invention, the spectrometer comprises displacement means for adjusting different relative positions of the photodiode array and the beam diffracted by the diffraction means such that the wavelength ranges intercepted by the photodiodes, respectively, can be varied in small steps. The wavelength range intercepted by a specific photodiode at a certain relative position of the photodiode array and the diffracted beam thus differs from the wavelength range intercepted by that photodiode at another relative position. The adjustment of different relative positions can be performed in such small steps that the wavelength intervals intercepted by a specific photodiode at two subsequent steps partially overlap. The spectrometer according to the invention permits a finer sampling of the diffracted beam than prior art photodiode array spectrometers wherein the wavelength range impinging on a specific photodiode always remains the same. The invention thus ensures improved spatial sampling of the diffracted beam and therefore, since different locations in the diffracted beam correspond to different wavelengths, improved spectral sampling, resulting in an improved spectral resolution of the spectrometer. The invention also ensures that diffracted rays which, at one relative position of the array and the diffracted beam, impinge on a gap between photodiodes, impinge on a photodiode at another relative position so that substantially all spectral information in the diffracted beam can be gathered, thus also contributing to an enhanced resolution.

The relative displacement of the photodiode array and the diffracted beam can be achieved in a plurality of ways. In one embodiment of the invention, the displacement means comprise a rotatable transparent plate in the beam path in front of the diffraction means, whereby the beam displacement is due to the refraction of the beam and can be adjusted by adjusting the angle of rotation of the plate. An advantage of this embodiment is that it can easily be implemented in a conventional photodiode array spectrometer without requiring a rearrangement of the already existing components of the spectrometer.

According to another embodiment of the invention, a rotatable mirror arranged in the beam path in front of the diffraction means can be used for effecting the beam displacement. If, according to a further embodiment of the invention, the spectrometer is used for analysing a sample contained in a sample cell arranged to receive radiation from a radiation source, the beam displacement can be achieved by rotating the sample cell in the beam path, thus effecting a displacement of the beam due to refraction at the front and rear faces of the cell.

According to another embodiment of the invention, the relative displacement can be achieved by mechanically displacing the photodiode array, e.g., with a piezoelectric drive.

For recording a spectrum, a predetermined number of relative positions of the diffracted beam and the photodiode array between an initial relative position and a final relative position are adjusted and for each such position all photodiodes of the photodiode array are read out and the values are stored. Preferably, the distance between the initial relative position and the final relative position is selected to be equal to the distance between the centres of adjacent photodiodes. In the embodiment of the invention wherein the diffracted beam is displaced and the array is kept at a fixed position, this means that the diffracted beam as a whole is shifted in a plurality of steps by that distance, and in the embodiment wherein the photodiode array is shifted and the diffracted beam remains stationary, this means that the total displacement path of the array is equal to the distance between adjacent photodiodes. In both cases, it is ensured by the adjustment of different relative positions of the diffracted beam and the array that the spectral information contained in the diffracted beam is completely scanned. For the generation of a spectrum, the thus obtained data values are associated with wavelength values corresponding to the position of the photodiode from which the data value has been derived, respectively.

If the spectrometer according to the invention is used for analysing a sample contained in a sample cell through which a polychromatic beam of radiation passes, it is preferred that the final spectrum is obtained by forming the difference between a first spectrum recorded with the sample being present in the sample cell and a blank spectrum without the presence of the sample in the sample cell, but with the other conditions being unchanged. In that way, it can be compensated for any modifications of the light beam introduced by the sample cell or a solvent in the cell such that the final spectrum only reflects the modification of the light by the sample itself.

In order to still further improve the resolution of the spectrometer, the spectrum can be further processed by performing a deconvolution of the spectrum utilising the transfer function of the spectrometer. The transfer function of the spectrometer can be calculated from the widths of the entrance slit and of the exit slit of the spectrometer, and from the dispersion and imaging properties of the diffraction means.

Subsequently, embodiments of the invention are explained in more detail with reference to the drawings.

Figure 1:
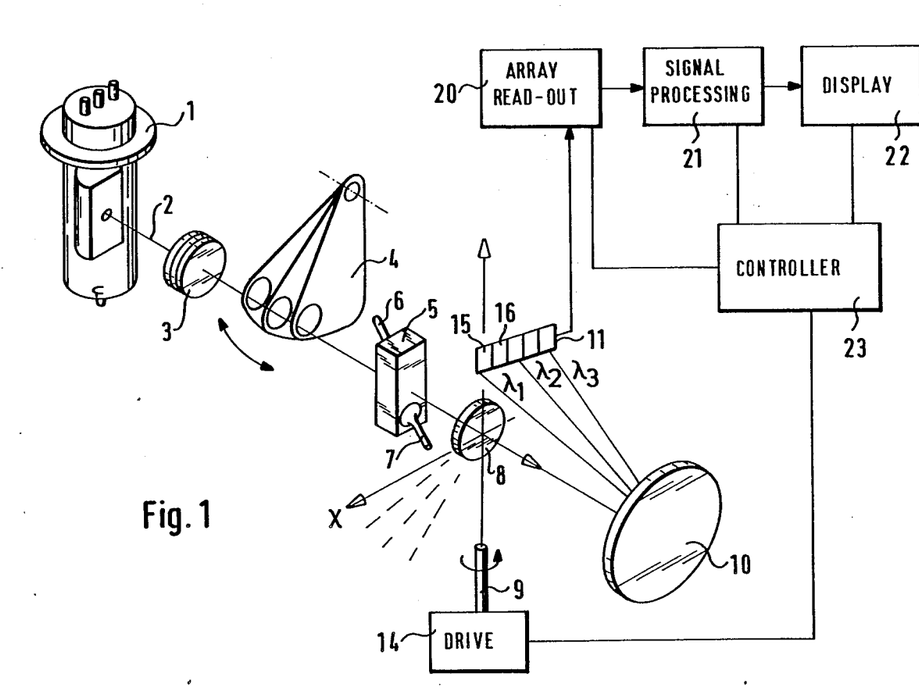
FIG. 1 is a schematic diagram of an embodiment of a photodiode array spectrometer according to the invention.

FIG. 1 schematically shows an embodiment a spectrometer according to the invention, which allows to measure the absorption of a polychromatic beam of ultraviolet or visible radiation by a sample to be analysed. The spectrometer comprises a light source 1, e.g., a deuterium lamp, which emits a beam 2 of polychromatic radiation. The beam 2 is focused by a lens system 3 into a sample cell 5. The lens system preferably is an achromatic system which ensures that rays of different wavelengths substantially have the same focal point. A shutter 4 is provided which permits to interrupt the light beam 2 in order to measure the dark signal at the photodiodes of the photodiode array 11. In the actual measuring process wherein the beam 2 passes through the sample cell 5, the dark signal and other electronic offset signals are subtracted from the measuring values to compensate for any measuring errors.

In the embodiment shown, the sample cell comprises an inlet 7 and an outlet 6 through which a sample liquid to be analysed flows continuously. The present spectrometer is particularly suited for use in a liquid chromatograph wherein the inlet 7 is connected to the chromatographic separation column from which sample substances are continuously eluting. It is understood, however, that the spectrometer according to the invention can advantageously be used for any application wherein a sample, either a liquid or a gas or a solid, is to be spectroscopically analysed.

The polychromatic radiation entering the sample cell 5 is partially absorbed by the substances in the cell, whereby, depending on the sample substances, rays of certain wavelengths are absorbed more strongly than rays of other wavelengths. As a result thereof, the beam leaving the cell has a different spectral composition than the beam entering the cell and the resulting spectrum thus contains information about the kind of substances in the cell and about their quantities.

The beam leaving the cell is transmitted through a plane-parallel glass plate 8. The glass plate can be rotated around an axis 9 by means of a motor 14 so that any desired angle between the direction of the beam 2 and the normal to the front face of the plate can be adjusted. If the front face of the glass plate is arranged such that the angle of incidence of the beam is equal to zero, the incident beam passes through the plate without deflection. If the plate is rotated away from such an angular position, the beam is refracted at the front face and at the rear face of the plate due to the differences in refracted indices at the glass/air interfaces. As a consequence thereof, the outgoing beam is displaced relative to the incoming beam. The displacement of the beam by the glass plate is explained in more detail below with reference to FIG. 2. The plate can be made, e.g., from the material Suprasil which is transparent over a wide range of wavelengths from the ultraviolet to the visible spectral range.

The beam from the glass plate 8 impinges on a holographic diffraction grating 10 which disperses the light according to the different wavelengths in the beam impinging on it. The spatially separated light rays from the grating 10 impinge on a photodiode array 11, which consists of a plurality of individual light-sensitive diodes 15, 16, etc., which are separated by light-insensitive gaps. Each of the photodiodes intercepts a specific spectral portion of the diffracted radiation. According to a typical example, the array 11 comprises 211 photodiodes with a center-to-center spacing of 61 micrometers and a gap width of 14 micrometers.

The photodiode array 11 is connected to a read-out circuit 20 for periodically reading out electrical signals from each of the photodiodes 15, 16, etc., whereby these signals are indicative of the intensity of the light signals impinging on the respective photodiode. The read-out circuit may be, for example, the read-out circuit used in the HP Model 1040A Spectrophotometric Detector (described in Hewlett-Packard Journal, April 1984, pages 31–41). The electrical signals from the photodiode array 11 are then further processed in a signal processing circuit 21 which typically comprises an analog-to-digital converter and circuitry for storing and further processing these digital values.

The signal processing circuit 21 also comprises circuitry for correcting the electrical signals from the individual photodiodes regarding the above-mentioned dark currents of the photodiodes and for other effects. Preferably, the final spectrum to be displayed on a display means 22 is derived by successively recording two intensity distributions (i.e., spectra), a first intensity distribution without sample in the sample cell, and a second intensity distribution with the sample cell being filled with the sample, and by electronically subtracting the two intensity distributions from each other. The thus obtained values form the final spectrum and are displayed in a single diagram on a display screen or in the form of a hardcopy. In such a diagram, the horizontal axis represents the wavelength of the diffracted light and the vertical axis represents the light intensity at the respective wavelengths or, according to an alternative graphical representation, the amount of light absorbed by the sample. An example of such a diagram is shown in FIG. 3.

The operation of the array read-out circuit 20, the signal processing circuit 21, and the display means 22 is controlled by a controller 23, typically comprising a microprocessor. The controller 23 also controls the angular setting of the rotatable plate 8 by providing corresponding control signals to the motor 14.

As can be seen from the embodiment shown in FIG. 1, a spectrometer according to the invention can be constructed by a comparatively small modification of a conventional photodiode array spectrometer, namely by adding a rotatable glass plate including corresponding drive and control means. For example, a spectrometer according to the invention can be obtained by providing the above-mentioned Hewlett-Packard Spectrophotometric Detector HP 1040A (described in Hewlett-Packard Journal, April 1984, pages 31–41) with a rotatable glass plate 8 as shown in FIG. 1 and by appropriately controlling the rotation of the plate and the remaining operation of the detector.

According to the embodiment of the invention shown in FIG. 1, the resolution of a spectrum is improved by reading out the photodiode array 11 at a plurality of angular settings of the rotatable glass plate 8 and by producing from all the read out signals a composite spectrum in a way to be described in more detail below. By adjusting the angular setting of the plate, the direction of the beam after passage through the plate can be adjusted. As a consequence thereof, the direction of the beam diffracted from the grating 10 towards the array 11 can also be adjusted, so that the diffracted beam scans the array in small steps resulting in an improved sampling of the spectral information contained in the diffracted beam.

Figure 2:
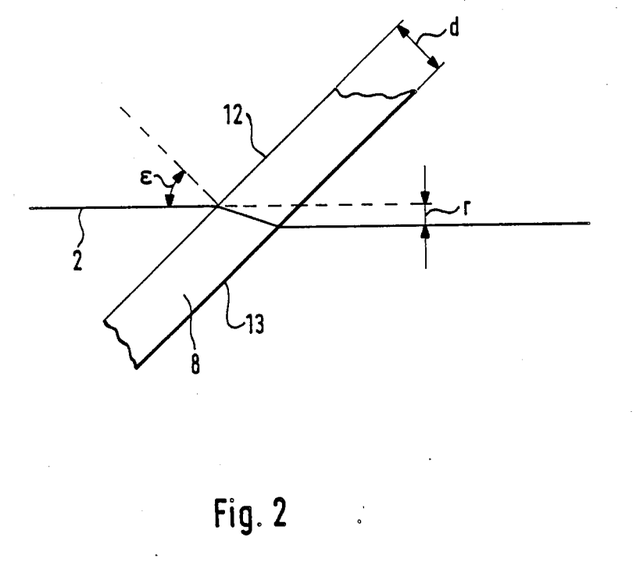
FIG. 2 illustrates the displacement of a light beam when passing through the glass plate shown in FIG. 1.

In the following, the shift of the beam 2 when passing through the plate 8 is explained with reference to FIG. 2. At the interface 12 between the surrounding air and the glass plate 8, the incoming beam 2 is refracted in dependence of the refractive indices of the plate and the environment and the angle of incidence. When leaving the plate 8, the beam is refracted again at the interface 13 so that the outgoing beam is parallely displaced with respect to the incoming beam by an amount r. According to the law of refraction, the displacement r is equal to:

$$r = \sin \epsilon \cdot d \cdot (n-1)/n, \tag{1}$$

whereby $\epsilon$ is the angle of incidence of the beam 2, d is the thickness of the plate 8, n is the refractive index of the plate, and 1 is the refractive index of air.

In an embodiment of the invention, the diffraction grating 10 is a concave grating which focuses the diffracted rays on the photodiode array 11 such that the image scale is 1, i.e., that the grating does neither magnify nor demagnify. For such a grating, any displacement r of the beam at the plate 8 as shown in FIG. 2 also occurs with the same amount at the photodiode array 11, so that the displacement of a diffracted ray at the photodiode array upon rotation of the plate 8 by a known angle $\epsilon$ can be calculated directly from equation (1).

For the purpose of illustration, the following example is to be considered. Assume that the grating generates a 1:1 imaging and that the center-to-center spacing between adjacent photodiodes in the photodiode array is 61 micrometers. If the total displacement r of an arbitrary ray diffracted from the grating and therefore of the whole beam 2 passing through the plate 8 is selected to be 61 micrometers, it is ensured that all diffracted rays impinge on a photodiode at some angular position of the plate. Using a glass plate with a thickness of 1.5 millimeters and a refractive index of 1.5, the corresponding angle by which the glass plate 8 has to be rotated from the position perpendicular to the beam 2 would be 7 degrees. This total angular range is covered in a plurality of angular steps and for each such step the photodiodes are read out and the corresponding data are stored. Considering the general case of a center-to-center spacing p of adjacent photodiodes and a step width s of the beam displacement at each step, the following equation has to be met to ensure complete scanning of the diffracted beam:

$$r \geq p - s \tag{2}$$

It is understood that the diffraction grating may have any imaging properties and is not limited to the 1:1 imaging as in the above example. It is furthermore understood that the diffraction means in a spectrometer need not be a grating but that any diffraction element, for example a prism, could be used.

Figure 3A:
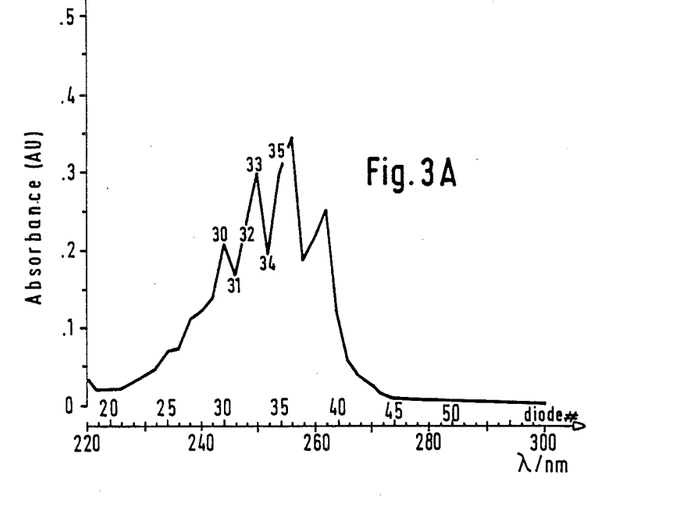
FIG. 3a shows a spectrum obtained with a prior art photodiode array spectrometer.
Figure 3B:
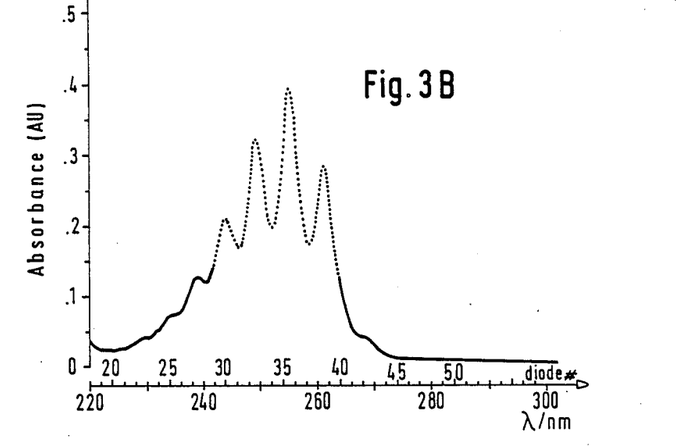
FIG. 3b shows a spectrum obtained with the spectrometer described with reference to FIGS. 1 and 2.

Subsequently, a typical procedure for recording a spectrum with the apparatus shown in FIG. 1 is described. For illustrating the procedure, reference is made to FIGS. 3a and 3b which show spectra for a sample of benzene, respectively. FIG. 3a shows a spectrum of a benzene sample obtained with a photodiode array spectrometer according to the prior art and FIG. 3b shows a spectrum of the same sample obtained with a photodiode array spectrometer according to the invention. The light source, the lens system, the sample cell, the grating and the photodiode array used in both cases are identical. In the graphical representations of FIGS. 3a and 3b, absorbance (unit: au) is plotted versus wavelength (unit: nm). Absorbance is a quantity representative of the amount of light absorbed by the sample at a specific wavelength. The plots shown in FIGS. 3a and 3b are typical for chromatographic applications wherein the sample in the sample cell has eluted from a chromatographic column.

The spectra in FIGS. 3a and 3b consist of a plurality of data points, whereby each such data point is derived by means of a signal processing circuit from the signal measured at a specific photodiode of the photodiode array. For example, the data points 31, 32, 33, 34 in FIG. 3a are derived from four adjacent photodiodes in the array. In the graphical representation of FIGS. 3a and 3b, the diode numbers are indicated above the horizontal (wavelength) axis. In FIG. 3a, the data points are connected with solid lines in order to provide a better graphical impression of the spectrum.

The spectrum shown in FIG. 3b is obtained in the following manner: In a first step, a reference or "blank" spectrum comprising a plurality of data points is derived and stored, whereby thee sample cell 5 does not contain the sample. In a second step, a sample spectrum is derived and stored, with the sample cell being filled with the sample. The number of data points of the sample spectrum is equal to the number of data points of the reference spectrum. Then, the difference of the two spectra is formed by subtracting for each data point the absorbance values of the data points of the blank spectrum from the absorbance values of the corresponding data points of the sample spectrum. The result is the spectrum shown in FIG. 3b.

The reference spectrum and the sample spectrum are obtained in the same manner by repeatedly performing the following steps: reading out all photodiodes of the array, processing the read out signals and storing the processed signals, and rotating the glass plate 8 by a small angle to a new angular position. In the example according to FIG. 3b, the glass plate 8 is rotated in 26 angular steps through a total angle of 7 degrees. Assuming a total number of n photodiodes of the photodiode array, n data points are recorded at each angular position of the plate 8. Since the plate is succesively positioned at 26 different angles, the total number of data points in the complete reference spectrum or the complete sample spectrum is 26 times n. For each new angular position of the plate 8, a specific photodiode intercepts a different portion of the beam from the grating 10 and consequently a different wavelength range. Thus, absorbance values can be derived at substantially more wavelengths than in a prior art photodiode array spectrometer, so that the spectral resolution is substantially enhanced. In the above-mentioned example, the number of data points can be increased by a factor of 26 as compared to the spectrum of FIG. 3a recorded with the spectrometer according to the prior art. For further illustration of the invention, consider the region of the spectrum of FIG. 3a between the data points 31 and 32: In the known photodiode array spectrometer, there are only two data points in this region, whereas in the spectrum shown in FIG. 3b, there are 26 data points in this region ensuring higher resolution. In the prior art spectrum of FIG. 3a, these two data points correspond to the signals derived from two adjacent photodiodes, whereas the mentioned 26 data points in the spectrum of FIG. 3b correspond to the signals derived from a single photodiode at 26 different angular positions of the plate 8.

Figure 1A:
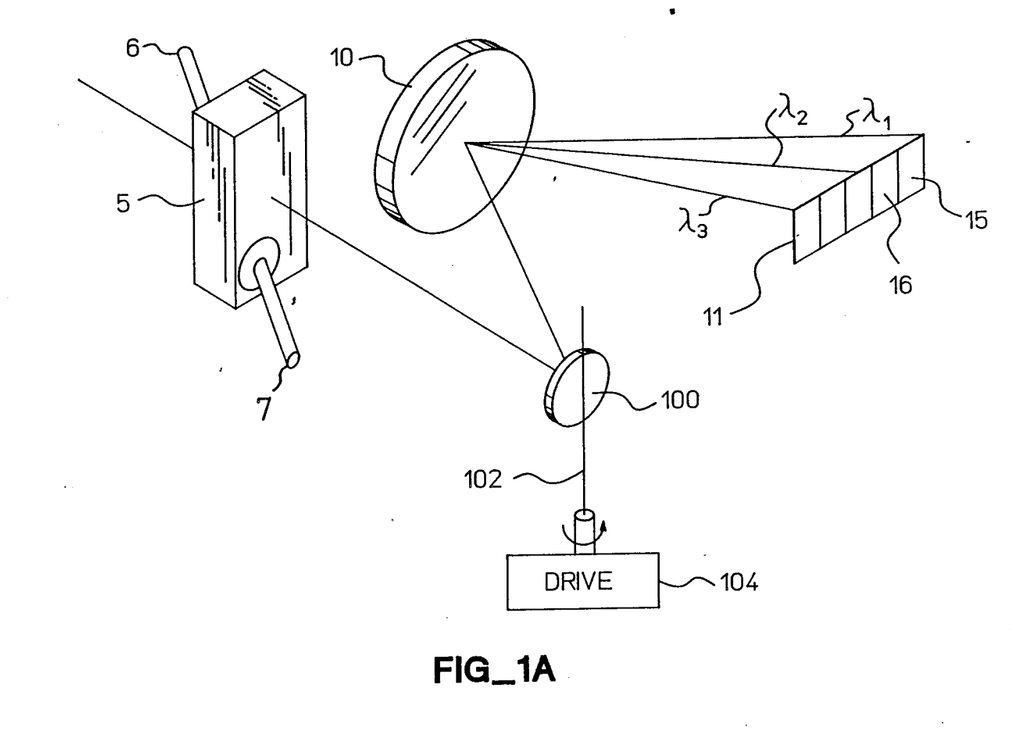
FIG. 1a is a partial schematic diagram of a first alternate embodiment of a displacement mechanism for a photodiode array spectrometer according to the invention.

In an alternative embodiment of the invention as illustrated in FIG. 1a, the displacement of the beam impinging on the diffraction means can be accomplished by means of a rotatable mirror 100 which can be rotated around an axis 102 by a drive 104, where the mirror 100 is arranged in the beam path between the sample cell and the diffraction means. The mirror reflects the beam transmitted from the sample cell to the diffraction means, whereby the beam displacement can be adjusted by adjusting the angle of rotation of the mirror.

Figure 1B:
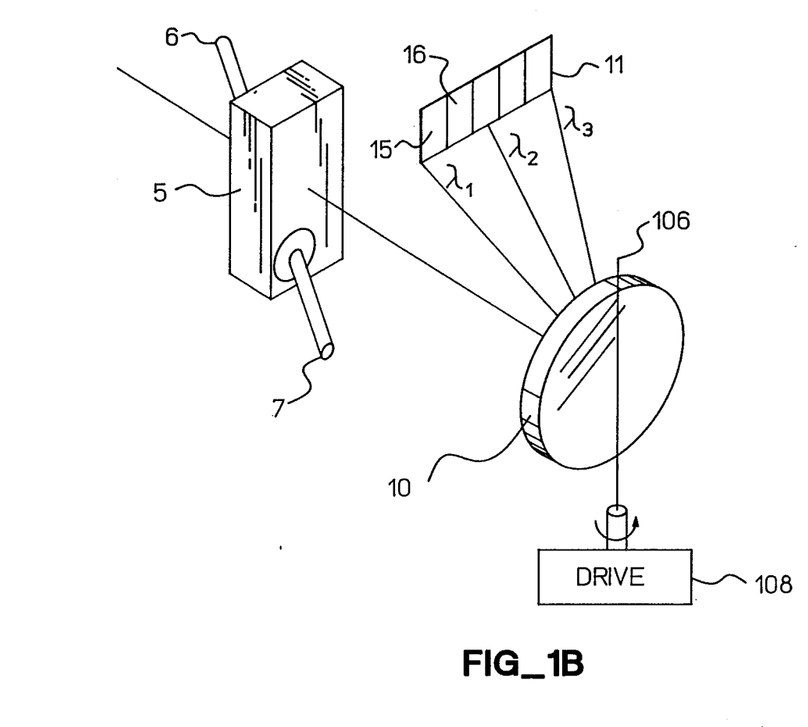
FIG. 1b is a partial schematic diagram of a second alternate embodiment of a displacement mechanism for a photodiode array spectrometer according to the invention.

In another embodiment as illustrated in FIG. 1b, the grating 10 itself can be rotatable around an axis 106 perpendicular to the array by a drive 108, so that the required beam displacement can be achieved by adjusting the angle of rotation of the diffraction means.

Figure 1C:
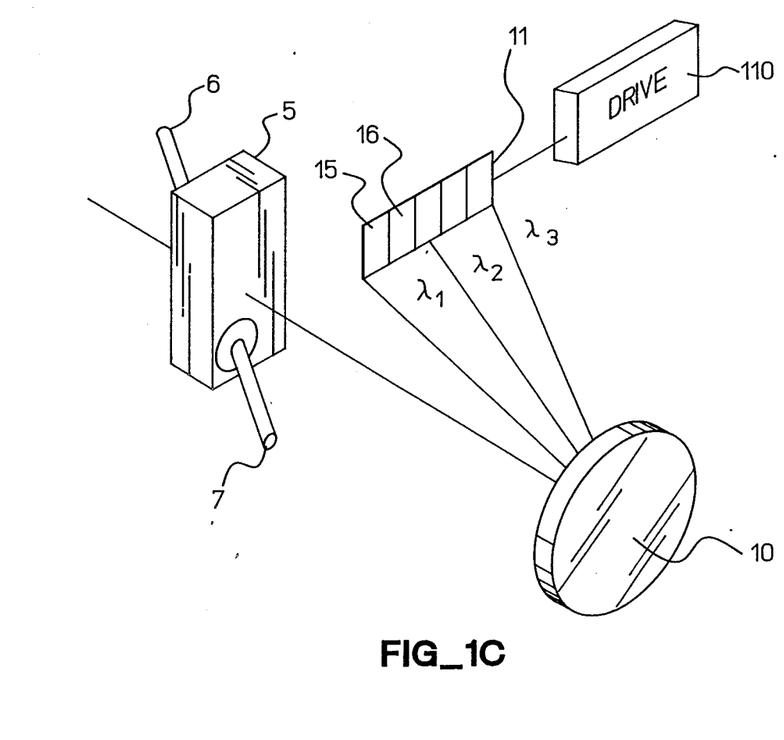
FIG. 1c is a partial schematic diagram of a third alternate embodiment of a displacement mechanism for a photodiode array spectrometer according to the invention.

According to still another embodiment of the invention as illustrated in FIG. 1c, the relative shift of the diffracted rays and the photodiode array is not accomplished by an additional optical element in the optical path in front of the array, but by displacing the array itself. In principle, such a displacement can be performed by any drive means 10 that permits to shift the whole array in small steps along a line, for example a stepping motor coupled to appropriate gears. Preferably, however, a piezoelectric element coupled to the photodiode array is used as drive means, because the displacement of such an element can be controlled in a simple way by applying a corresponding voltage. The procedure for recording a spectrum is substantially the same as the one described in the above-mentioned embodiment, with the exception that instead of a stepwise rotation of a glass plate, there is a stepwise linear displacement of the array 11.

It is understood that a spectrometer according to the invention can be used for determining the spectral composition of any kind of electromagnetic radiation, for example radiation in the visible or in the ultraviolet or in the infrared spectral range, provided the photodiodes of the array are sensitive in these spectral ranges, respectively.

It is furthermore understood that the principle of the invention can generally be used for improving the resolution in the scanning of a spatial radiation distribution with a photodiode array.

We claim:

1. A photodiode array spectrometer for determining the spectral composition of a polychromatic beam of radiation comprising:
    diffraction means for receiving the polychromatic beam of radiation and for generating therefrom a diffracted beam comprising a plurality of spatially separated diffracted rays of different wavelengths;
    a photodiode array for receiving at least a portion of the diffracted beam, with the array comprising a plurality of photodiodes intercepting different wavelength ranges of the diffracted beam, each wavelength range comprising a plurality of diffracted rays of different wavelengths;
    displacement means for adjusting, in a plurality of discrete steps, the relative position of said diffracted beam and said photodiode array such that a majority of said diffracted rays that are received by said photodiode array impinge upon at least one photodiode at some relative position; and
    processing means coupled to said photodiode array for receiving and processing a plurality of spectral signals corresponding to said plurality of discrete steps.

2. A photodiode array spectrometer according to claim 1, wherein said displacement means includes a transparent planeparallel plate for receiving said polychromatic beam of radiation and transmitting the polychromatic beam towards said diffraction means, said plate being rotatable around an axis to displace said polychromatic beam by an amount which is dependent on the angular orientation of the plate.

3. A photodiode array spectrometer according to claim 1, wherein said displacement means includes a control arrangement coupled to said photodiode array for controllably shifting said photodiode array in said plurality of discrete steps.

4. A photodiode array spectrometer according to claim 3, wherein said control arrangement includes a piezoelectric element.

5. A photodiode array spectrometer according to claim 1, wherein said displacement means includes an adjustably rotatable mirror arranged to receive said polychromatic beam and to reflect said polychromatic beam towards said diffraction means in said plurality of discrete steps.

6. A photodiode array spectrometer according to claim 1 further comprising control means for controlling the displacement means to enable adjustment of relative positions of said diffracted beam and the photodiode array in said discrete steps within a range approximately equal to the distance between the centers of adjacent photodiodes of said photodiode array.

7. A photodiode array spectrometer according to claim 1 further comprising control means for performing a deconvolution of a recorded spectrum in accordance with a predetermined transfer function.

8. A photodiode array spectrometer according to claim 1 wherein said displacement means includes means for changing the angular orientation of said diffraction means relative to said polychromatic beam in said plurality of discrete steps.

* * * * *